US010273037B2

(12) United States Patent
Pan et al.

(10) Patent No.: US 10,273,037 B2
(45) Date of Patent: Apr. 30, 2019

(54) REUSABLE PACKAGING AND STORAGE

(71) Applicant: Reckitt Benckiser (Brands) Limited, Slough (GB)

(72) Inventors: Kevin Pan, Dongguan (CN); Piotr Zaborniak, Hull (GB); Teun Franciscus van Wetten, Eindhoven (NL)

(73) Assignee: RECKITT BENCKISER (BRANDS) LIMITED, Slough (GB)

( * ) Notice: Subject to any disclaimer, the term of this patent is extended or adjusted under 35 U.S.C. 154(b) by 0 days.

(21) Appl. No.: 15/546,632

(22) PCT Filed: Jan. 27, 2016

(86) PCT No.: PCT/GB2016/050171
§ 371 (c)(1),
(2) Date: Jul. 26, 2017

(87) PCT Pub. No.: WO2016/120613
PCT Pub. Date: Aug. 4, 2016

(65) Prior Publication Data
US 2018/0022496 A1 Jan. 25, 2018

(30) Foreign Application Priority Data
Jan. 30, 2015 (GB) .................................. 1501578.7

(51) Int. Cl.
*B65D 1/24* (2006.01)
*A61F 5/41* (2006.01)
(Continued)

(52) U.S. Cl.
CPC .................. *B65D 1/24* (2013.01); *A61F 5/41* (2013.01); *A61F 6/005* (2013.01);
(Continued)

(58) Field of Classification Search
CPC ........ B65D 1/24; B65D 51/16; B65D 43/162; B65D 43/044; B65D 75/326; A61F 5/41;
(Continued)

(56) References Cited

U.S. PATENT DOCUMENTS 4,289,232 A 9/1981 Seibel et al.
4,605,127 A * 8/1986 Magnussen, Jr. ...... B65D 77/26
206/493
(Continued)

FOREIGN PATENT DOCUMENTS

DE 3237566 A1 4/1984
FR 1038953 A 10/1953
FR 2767119 A1 2/1999

OTHER PUBLICATIONS

Combined Search and Examination Report issued in corresponding Great Britain Application No. GB1501578.7 dated Aug. 6, 2015.
(Continued)

*Primary Examiner* — Jacob K Ackun
*Assistant Examiner* — Jenine Pagan
(74) *Attorney, Agent, or Firm* — Troutman Sanders LLP; Ryan Schneider; Chris Davis

(57) ABSTRACT

A reusable packaging and storage article for an elastic constriction ring is described wherein the article comprises a top member and a bottom member configured to releasably engage with each other, wherein the bottom member comprises: a cavity of substantially circular shape having a perimeter lip with an inner and outer surface to house, in use, a portion of the elastic constriction ring; and an at least partially pillar extending from a substantially central portion of the cavity; and wherein a summit of the pillar has a diameter less than the diameter of a central aperture of the elastic constriction ring, and a lower portion of the pillar has a diameter greater than the diameter of a central aperture of the elastic constriction ring; and wherein the top member
(Continued)

comprises: a cavity of substantially circular shape having a perimeter lip with an inner and outer surface to house, in use, a portion of the elastic constriction ring, wherein the diameter of an inner surface of the perimeter is the same or greater than the diameter of the outer surface of the perimeter lip of the bottom member. A consumer product is also described.

13 Claims, 2 Drawing Sheets

(51) Int. Cl.
| | |
|---|---|
| *A61F 6/00* | (2006.01) |
| *B65D 43/16* | (2006.01) |
| *B65D 75/32* | (2006.01) |
| *B65D 43/02* | (2006.01) |
| *B65D 51/16* | (2006.01) |

(52) U.S. Cl.
CPC ....... *B65D 43/0214* (2013.01); *B65D 43/162* (2013.01); *B65D 51/16* (2013.01); *B65D 75/326* (2013.01); *A61F 2005/414* (2013.01); *Y02W 30/807* (2015.05)

(58) Field of Classification Search
CPC .... A61F 2005/414; A61F 6/005; A45C 11/00; Y02W 30/807
USPC ..... 206/303, 69, 37, 38, 461, 462, 470, 471, 206/493; 220/834, 839
See application file for complete search history.

(56) References Cited

U.S. PATENT DOCUMENTS

| | | | | |
|---|---|---|---|---|
| 4,825,686 | A | | 5/1989 | Marsh |
| 5,456,379 | A | * | 10/1995 | Krupa ................ B65D 43/162 206/508 |
| 5,638,949 | A | | 6/1997 | Jones |
| 5,862,908 | A | | 1/1999 | Arbin |
| 5,878,881 | A | * | 3/1999 | Hunt ..................... A47L 13/51 15/184 |
| 5,896,983 | A | * | 4/1999 | Wood .................. A47G 25/904 128/844 |
| 6,129,088 | A | | 10/2000 | Favre |
| 9,096,372 | B2 | * | 8/2015 | Vulpitta ............... B65D 85/672 |
| 2007/0023303 | A1 | * | 2/2007 | Templeton ........... B65D 43/162 206/318 |
| 2015/0001106 | A1 | * | 1/2015 | Chopdat ................ A61F 6/005 206/205 |

OTHER PUBLICATIONS

Examination Report issued in corresponding Great Britain Application No. GB1501578.7 dated Jun. 26, 2017.
International Search Report and Written Opinion issued in corresponding PCT International Application No. PCT/GB2016/050171 dated Mar. 17, 2016.

* cited by examiner

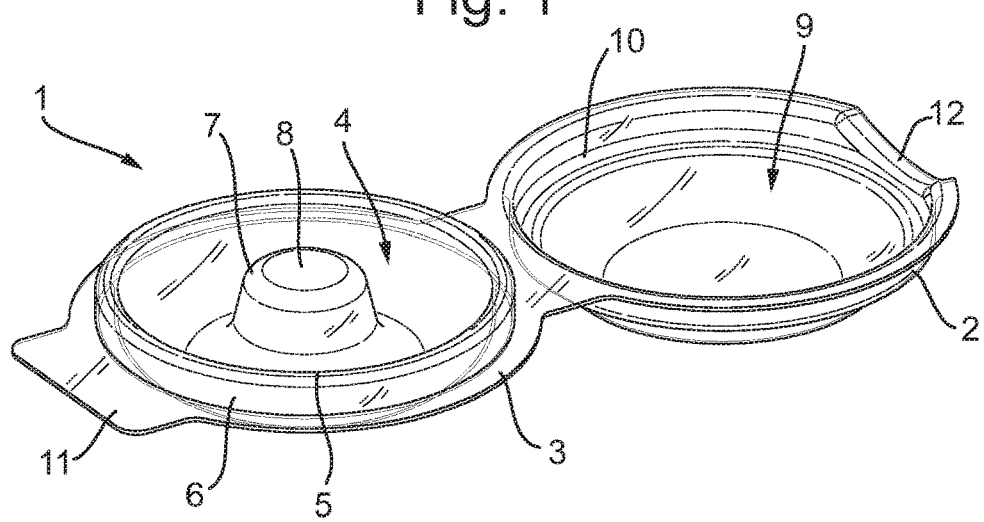
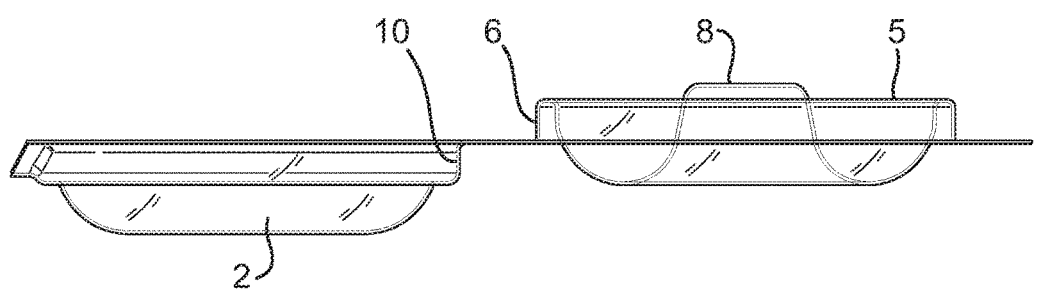
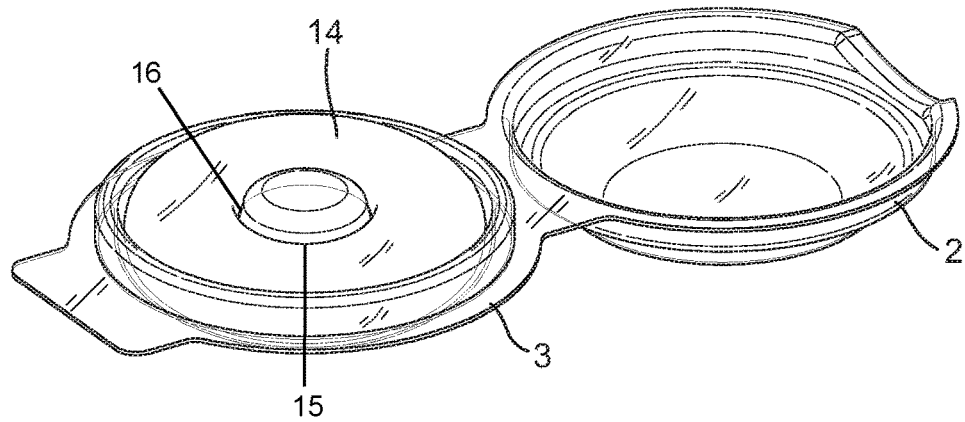

REUSABLE PACKAGING AND STORAGE

FIELD OF THE INVENTION

The invention relates to a reusable packaging and storage article and particularly, but not exclusively, a reusable packaging and storage article for the packaging and storage of an elastic constriction ring.

BACKGROUND

It is well known that providing a constriction at the base of a penis helps to maintain a longer and firmer erection and, to this end, elastic constriction rings are commonly used to facilitate such a constriction. Elastic constriction rings are typically intended to be reused and therefore they can be problematic to clean and keep clean after their first use until subsequent re-use.

The reusable packaging and storage article is intended to address such drawbacks.

SUMMARY OF INVENTION

According to a first aspect of the present invention there is provided therefore a reusable packaging and storage article for an elastic constriction ring comprising a top member and a bottom member configured to releasably engage with each other, wherein the bottom member comprises: a cavity of substantially circular shape having a perimeter lip with an inner and outer surface to house, in use, a portion of the elastic constriction ring; and a pillar extending from a substantially central portion of the cavity; and wherein a summit of the pillar has a diameter less than the diameter of a central aperture of the elastic constriction ring, and a lower portion of the pillar has a diameter greater than the diameter of a central aperture of the elastic constriction ring; and wherein the top member comprises: a cavity of substantially circular shape having a perimeter lip with an inner and outer surface to house, in use, a portion of the elastic constriction ring, wherein the diameter of an inner surface of the perimeter is the same or greater than the diameter of the outer surface of the perimeter lip of the bottom member.

The point at which the pillar is provided with a diameter equal to the diameter of the of the central aperture of the elastic constriction ring is hereinafter termed the impingement point and is the point at which, in use, an inner surface of the aperture in the elastic constriction ring makes contact with the pillar to secure the ring in frictional engagement with the pillar. Preferably the pillar is configured with the impingement point being located on the pillar such that, in use, a bottom surface of the elastic constriction ring is suspended above an upper surface of the cavity of the bottom member. This arrangement may be advantageous as it can promote airflow around a portion of the ring to permit effective drying thereof post-cleaning.

The pillar may be conical or pyramidal in shape. Preferably the pillar is frusto-conical in shape. Preferably the pillar is widest at its base adjacent the cavity from which it extends.

The cavity in the bottom portion preferably defines a tubular shape which corresponds to the tubular shape of the elastic constriction ring.

The perimeter lip of the bottom member is preferably at the same height or closer to the base of the cavity than the impingement point. This arrangement may be advantageous as, in use, when the top member and bottom member are disengaged from each other, the article is in the open position, the ring is held on the pillar by frictional force at the impingement point and the low height of the perimeter lip of the bottom member presents a large surface area of the ring thus making it easier user for a user to grab the ring and remove same from the pillar.

Preferably the perimeter lip of the top member is provided with a height that is substantially the same as the height of the perimeter lip of the bottom member such that when the top member and bottom member are engaged with each other, when the article is in the closed position, the perimeter lip of the bottom member can be secured within and adjacent to the perimeter lip of the top member.

Most preferably the perimeter lips of both the bottom member and the top member are sized to form frictional contact with each other when the top member and the bottom member are engaged with each other and the article is in the closed position, and particularly preferably said frictional contact between the perimeter lips is sufficient to provide a closure mechanism to releasably retain said members engaged with each other until a user applies a separating force to overcome said frictional contact and disengage said members and expose the cavities of the members.

Alternatively or additionally a separate closure mechanism may be provided to retain the top member and the bottom member in an engaged relationship.

The top member and/or bottom member may be provided with one or more vent holes. The vent holes may be advantageous to allow moisture to drain away from the ring post-cleaning.

Preferably the article is made as a single piece, preferably from a plastics material that may be injection-moulded or thermoformed. When made as a single piece the top member and bottom member may be provided in a clamshell arrangement.

According to a second aspect of the present invention there is provided therefore a consumer product comprising a reusable packaging and storage article and an elastic constriction ring;

wherein the article comprises a top member and a bottom member configured to releasably engage with each other, wherein the bottom member comprises: a cavity of substantially circular shape having a perimeter lip with an inner and outer surface to house, in use, a portion of the elastic constriction ring; and a pillar extending from a substantially central portion of the cavity; and wherein a summit of the pillar has a diameter less than the diameter of a central aperture of the elastic constriction ring, and a lower portion of the pillar has a diameter greater than the diameter of a central aperture of the elastic constriction ring; and wherein the top member comprises: a cavity of substantially circular shape having a perimeter lip with an inner and outer surface to house, in use, a portion of the elastic constriction ring, wherein the diameter of an inner surface of the perimeter is the same or greater than the diameter of the outer surface of the perimeter lip of the bottom member; and wherein the elastic constriction ring comprises a tubular ring of resilient elastic material.

BRIEF DESCRIPTION OF THE DRAWINGS

Embodiments of the invention will now be described, by way of example only, with reference to the following drawings in which:

FIG. 1 illustrates a perspective view of the article in an open configuration without a constriction ring inserted;

FIG. 2 illustrates a side view of the article in an open configuration without a constriction ring inserted;

FIG. 3 illustrates a perspective view of the article in an open configuration with a constriction ring inserted;

DESCRIPTION OF AN EMBODIMENT

Figure 4:
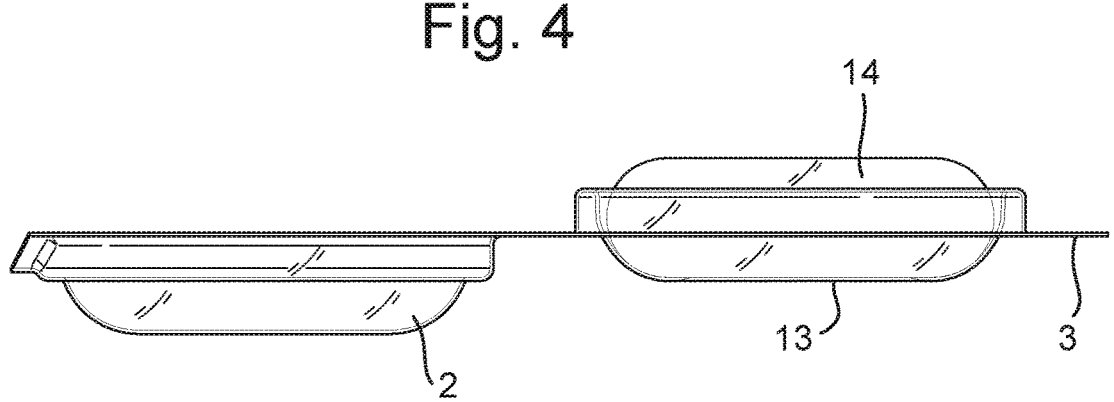
FIG. 4 illustrates a side view of the article in an open configuration with a constriction ring inserted.

FIGS. 1&2 illustrate a reusable packaging and storage article 1 suitable for packaging and storing an elastic constriction ring 14. The article 1 is made in one-piece having a top member 2 and a bottom member 3. The bottom member 3 has a cavity 4 of substantially tubular circular shape. At the perimeter of the cavity 4 is a perimeter lip 5 which has a flat outer surface 6. From a substantially central portion of the cavity extends a pillar 7. The pillar 7 is at least partially conical and is shown as frusto-conical with the widest part of the pillar 7 being adjacent a base of the cavity 4 and culminating in a flat summit 8. As can be seen in FIG. 2 the summit 8 has a greater height than the height of the perimeter wall 5.

The top member 2 is provided with a cavity 9 having a circular shape which is configured to accommodate a proportion of the elastic constriction ring 14 and pillar 7. The cavity 9 is provided with a perimeter lip 10 having a flat inner surface. The diameter of the flat inner surface of perimeter lip 10 is the same or fractionally greater than the diameter of the flat outer surface of the perimeter lip 6 of the bottom member 3. Such proximity of diameters permits the lips 6,10 to form frictional contact with each other when the top member 2 is brought into engagement with the bottom member 3 in the closed position, as shown in FIG. 5. The frictional contact between the perimeter lips 6, 10 is sufficient to provide a closure mechanism to releasably retain said members 2,3 engaged with each other until a user applies a separating force to overcome said frictional contact and disengage said members 2,3. The bottom member 3 is provided with a tab 11 which, when the article 1 is in the closed position as shown in FIG. 5, corresponds with a recessed portion 12 in the perimeter lip 10 to improve the ability for a user to form a firm grip of each member 2,3 to separate them to place the article in the open position as shown in FIGS. 1-4.

Figure 5:
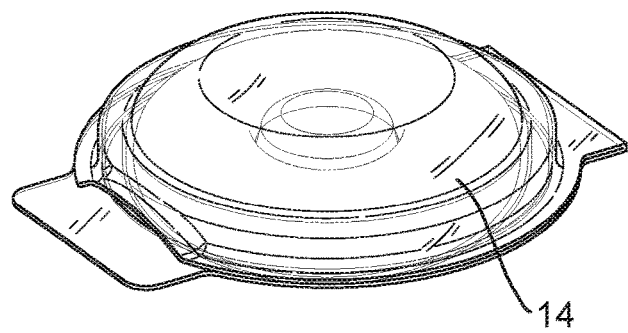
FIG. 5 illustrates a perspective view of the article in a closed configuration with a constriction ring inserted.

As can be seen in FIGS. 3-5, the ring 14 does not touch the base of the cavity 4, instead the ring is suspended above said base. As the summit 8 of the pillar 7 has a diameter less than the diameter of a central aperture 15 of the elastic constriction ring 1 and a lower portion of the pillar 7 has a diameter greater than the diameter of a central aperture 15 of the elastic constriction ring 14, there is an impingement point 16 between the pillar 7 and the central aperture 15 of the ring which is configured to ensure that the ring 14 is suspended above the base of the cavity 4 when mounted by frictional engagement on the pillar 7 at the impingement point 16. This arrangement can promote airflow around a portion of the ring to permit effective drying thereof post-cleaning.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A consumer product comprising:
a reusable article which is a packaging and storage article having a top member and a bottom member configured to releasably engage with each other; and
an elastic constriction ring having a central aperture and comprising a tubular ring of resilient elastic material;
wherein the bottom member comprises:
a cavity of substantially circular shape having a perimeter lip with an inner and outer surface to house, in use, a portion of the elastic constriction ring; and
a pillar extending from a substantially central portion of the cavity of the bottom member;
wherein a summit of the pillar has a diameter less than the diameter of the central aperture of the elastic constriction ring, and a lower portion of the pillar has a diameter greater than the diameter of the central aperture of the elastic constriction ring;
wherein the pillar is configured with an impingement point such that, in storage of the elastic constriction ring in the article, a bottom surface of the elastic constriction ring is suspended above an upper surface of the cavity of the bottom member; and
wherein the top member comprises:
a cavity of substantially circular shape having a perimeter lip with an inner and outer surface to house, in use, a portion of the elastic constriction ring;
wherein the diameter of an inner surface of the perimeter lip of the top member is the same or greater than the diameter of the outer surface of the perimeter lip of the bottom member.

2. The consumer product according to claim 1, wherein the cavity of the bottom portion defines a tubular shape.

3. The consumer product according to claim 1, wherein the perimeter lip of the bottom member is at the same height as the impingement point of the pillar.

4. The consumer product according to claim 1, wherein the perimeter lip of the top member is provided with a height that is substantially the same as the height of the perimeter lip of the bottom member such that when the top member and bottom member are engaged with each other when the article is in a closed position, the perimeter lip of the bottom member is secured within and adjacent to the perimeter lip of the top member.

5. The consumer product according to claim 1, wherein the perimeter lips of both the bottom member and the top member are sized to form frictional contact with each other when the top member and the bottom member are engaged with each other and the article is in a closed position.

6. The consumer product according to claim 5, wherein the frictional contact between the perimeter lips is sufficient to provide a closure mechanism to releasably retain the top and bottom members in the closed position.

7. The consumer product according to claim 1, wherein one or both of the top member and the bottom member is provided with one or more vent holes.

8. The consumer product according to claim 1, wherein the article is made as a single piece construction.

9. The consumer product according to claim 8, wherein the article is made of a plastic material.

10. The consumer product according to claim 9, wherein the article is injection moulded, blow-moulded or thermo-formed.

11. The consumer product according to claim 1, wherein the pillar is conical or frusto-conical in shape.

12. The consumer product according to claim 11, wherein the pillar is frusto-conical in shape.

13. The consumer product according to claim 1, wherein the elastic constriction ring consists of the tubular ring of resilient elastic material.

* * * * *